United States Patent [19]

Audonnet et al.

[11] Patent Number: 5,676,952
[45] Date of Patent: Oct. 14, 1997

[54] HERPESVIRUSES TRANSFORMED TO EXPRESS GD IN VITRO

[75] Inventors: **Jean-Christophe Francis Audonnet; Raphaël Jean Dar

HERPESVIRUSES TRANSFORMED TO EXPRESS GD IN VITRO

The present invention relates to new recombinant herpesviruses obtained from herpesviruses naturally deficient in gD, in particular alphaherpesviruses and avian herpesviruses, especially avian alphaherpesviruses and more especially serotypes 1, 2 and 3 MDV, as well as, in particular VZV. It also relates, inter alia, to their use as vaccines and to a method for preparing them.

The virus responsible for Marek's disease (Marek's disease virus or MDV) in chickens is an alphaherpesvirus. Three serotypes of the MDV virus are described (Bülow V. V. and Biggs P. M., Avian Pathology, 1975, 4, 133–146). Only the oncogenic serotype 1 viruses are pathogenic in chickens. Their replication in the host causes the formation of T cell lymphomas and a demyelination of the peripheral motor nerves reflected, in general, in signs of paresia or of paralysis in affected animals (Calnek and Witter, Marek's Disease in Diseases of Poultry 9th edition, pp 342–390, Calnek B. W. et al. Ed. 1991, Iowa State Univ. Press). This disease, the economic consequences of which are very serious for poultry breeding, is prevented by a vaccination of day-old chicks with either turkey herpesvirus (Herpesvirus of turkey or HVT, or alternatively serotype 3 MDV), a virus antigenically close to the MDV virus but non-pathogenic in chickens, or live MDV strains which are non-oncogenic and non-pathogenic in chickens, belonging to serotypes 1 or 2.

For the requirements of vaccine production, these three serotypes are mainly cultured on primary chick embryo cells (CECs). Primary duck embryo cells may also be used to multiply serotype 2 MDV viruses. During culture in vitro, these viruses are strongly cell-associated. This phenomenon has been known for a long time (Churchill A. E. and Biggs P. M. Nature, 1967, 215, 528–530), and it was also found that the virions produced after culture on CECs were non-infectious via the oral or nasal route for chickens. Vaccination with these viruses hence requires them to be administered parenterally, in general by transfixing the alar membrane or by intra-muscular injection, thereby increasing the cost of vaccination against Marek's disease to a not insignificant extent.

There is, on the other hand, in chickens, a production of infectious MDV virus, that is to say which can be transmitted aerially or by simple contact, during infection by pathogenic strains of MDV virus. This production of infectious virus takes place in the feather follicles, and the virus is disseminated in the environment via moult feathers, squamae and dusts (Calnek B. W. et al., Avian Diseases, 1970, 14, 219–233). This is the mechanism whereby the natural spread of the disease takes place on farms. The differences observed between the in vitro culture and in vivo replication of the MDV virus have never yet been explained.

A study of the in vitro culture of HVT or MDV viruses on CECs showed that these viruses were closely associated with the cell membranes. The outcome of this is the virtual absence of free and infectious virions in the culture supernatants.

It has just been shown recently that a gene coding for a glycoprotein homologous with HSV-1 gD is present on the respective genomes of the HVT and MDV viruses (Ross L. J. N. et al., J. Gen. Virol. 1991, 72, 949–954; Zelnik V. et al., J. Gen. Virol. 1993, 74, 2151–2162). The expression products of these genes in HVT and MDV have been studied and looked for in the lysates of CECs infected with these viruses. These experiments have not, however, enabled the expression of the gD glycoprotein to be demonstrated in these two viruses.

In effect, MDV gD antigens, expressed in the form of fusion proteins with the TrpE protein in E. coli, were used to induce antibody production in rabbits and, curiously, the sera thus prepared did not recognize a specific protein in the lysates of CECs infected with HVT or MDV, whereas the antibodies prepared from fusion proteins expressing MDV gI or MDV gE antigens recognize the corresponding glycoproteins expressed by the MDV or HVT viruses during culture in vitro (Brunovskis P. et al., Proceedings 19th World's Poultry Congress, pp. 118–122. Amsterdam, 19–24 September 1992). This indicates either an absence of expression or a very low level of expression of gD during in vitro culture of HVT and MDV.

In contrast, sera of chickens infected with pathogenic strains of MDV recognize the HVT gD or MDV gD antigens expressed in the form of fusion proteins with glutathione transferase (Zelnik V. et al., Proceedings 19th World's Poultry Congress, pp. 114–117. Amsterdam, 19–24 September 1992). These results show that the HVT gD and MDV gD genes are indeed expressed during in vivo replication in chickens, and that the respective glycoproteins are not only immunogenic but also share some antigenic determinants. It should be noted that, in most alphaherpesviruses studied to date, the gD glycoprotein is a major immunogen which contributes significantly to the induction of antiviral protective immunity in the infected or immunized animal.

X. Tan and L. F. Velicer (Abstracts of the XVIII International Herpesvirus Workshop, University of Pittsburgh Medical Center, Pittsburgh, Pa. 1993, p. A145) have also declared that gD was not expressed in cell culture, or at least not at a level detectable by Northern blotting, which might explain the cell-associated nature of the MDV virus. These authors propose that MDV gD is expressed in the epithelium of chicken feather follicles, where MDV is formed in the form of non-cell-associated enveloped infectious virions.

The present invention is based on the discovery that the implementation of a constitutive expression of the gD glycoprotein by the MDV virus, including HVT, surprisingly enables non-cell-associated free virions to be obtained as occurs during infection in chickens. This feature affords the very advantageous possibility of administering this virus aerially for vaccinal purposes, and enables, moreover, free virus to be obtained in the supernatant of in vitro cultures, thereby making it easier to obtain and manufacture the vaccine against Marek's disease.

Surprisingly, by replacement of the natural promoter of the gD gene in the HVT and MDV viruses by another promoter, the present invention permits the in vitro expression of the HVT gD and MDV gD glycoproteins. The expression of gD, obtained, in particular, by placing this gene under the control of a promoter not regulated by the virus, permits complete maturation of the virions, which can then "exit" freely from the infected cells. This expression of gD in vitro is achieved by replacing the natural promoter of the gD gene by another promoter which can be chosen, in particular, from traditionally known strong eukaryotic promoters, for example HCMV IE, SV40 promoters, or endogenous early promoters of the HVT or MDV viruses, etc.) or late promoters (for example MDV or HVT late promoters, in particular of MDV or HVT gB, etc.). This novel expression may be obtained using the means afforded by genetic recombination techniques, by replacing, for example, the region located upstream of the ATG of the gD gene by an exogenous promoter of the HCMV IE or SV40 type, or by transposing the gD gene into the long unique region of the virus and placing it under the control of an endogenous or exogenous promoter. Many possibilities can thus be realized for expression of the gD gene, by combining different promoters and different potential insertion sites (such as the RR2, TK, gD, gI, US3, US2, US10, etc., sites).

This expression has novel and unexpected repercussions on the biological properties of the recombinant virus. Expression of the gD glycoprotein during the in vitro replication of the recombinant HVT and MDV viruses thus constructed manifests itself, in effect, in the incorporation of the gD glycoprotein into the viral envelope and in the obtaining of infectious virions at a high titre in the culture supernatants. Moreover, the recombinant viruses thereby obtained, while retaining the attenuation characteristics of the parent viruses, are more infectious for lymphocytes in vivo and replicate more rapidly in these cells. The direct outcome of this is a greater and more rapid diffusion of these viruses within the chicken's body. Protection against Marek's disease is hence better, irrespective of the administration route (oronasal or parenteral). As a result of these biological modifications in replication of the virus, protection against Marek's disease may be obtained earlier and with much smaller vaccine doses than with the vaccines traditionally used.

It was, in addition, discovered that it was possible to extend this teaching to other herpesviruses whose genomic structure and in vitro and in vivo biological properties are equivalent to those of the arian herpesviruses mentioned above. For example, the present invention enables a recombinant VZV virus expressing the gD gene of another virus such as HSV-1 or HSV-2 to be obtained, with the very advantageous outcome of the production of free VZV virus by in vitro culture on cells. This recombinant virus can constitute a vaccine against VZV and against the virus from which the gD gene originates, for example HSV-1 or HSV-2.

There are, in fact, two major types of virus to which the invention relates, which correspond to the definition of gD-deficient virus, namely those which do not express gD in vitro in cell cultures, as is the case with the MDV viruses, including HVT, and those which lack a gene homologous with the gD gene, as is the case with the VZV virus (varicella-zoster virus).

The invention hence relates to all herpesviruses which are equivalent, in the sense which has just been defined, to the model viruses MDV and VZV.

The subject of the present invention is hence a herpesvirus naturally deficient in gD (in the sense of the invention defined above), transformed to express a gD glycoprotein during its replication in vitro. Preferably, the virus in question is an avian herpesvirus, in particular serotypes 1, 2 and 3 MDV virus, or alternatively the varicella virus VZV.

According to a first preferred embodiment of the invention, which relates to herpesviruses having a gD gene not expressed in vitro, the herpesvirus has its gD gene placed under the control of a promoter other than the natural promoter of this gene. The natural promoter of the gD gene is replaced by an endogenous promoter (that is to say a promoter of this virus or of other serotypes of this virus, in particular an early promoter) or exogenous promoter, permitting expression of the gD gene in vitro.

In a second preferred embodiment of the invention, the herpesvirus comprises an expression cassette containing the gD gene placed under the control of a promoter permitting its expression during replication of the virus in vitro.

In the case of a herpesvirus not naturally possessing a gD gene, the cassette comprises the gD gene of another virus, for example of HSV or even of a virus such as MDV, including HVT, and a suitable promoter which can be the natural promoter of the gene inserted or be another promoter, which will be the case when the gD gene originates from an MDV type virus, the condition being to obtain an expression of the gD gene in vitro.

In the case of a herpesvirus deficient only in the expression of gD in vitro, the cassette can also comprise equally well the endogenous gD gene or another gD gene, and a suitable promoter as defined above.

The expression cassette is inserted into a site which is non-essential for the replication of the virus and for the efficacy of the virus as a vaccine. For serotypes 1, 2 and 3 MDV viruses, an insertion site is advantageously chosen from the group consisting of US2, US3, US10, gI, gD, TK, RR2, UL13. It will naturally be understood that this list is not limiting and that any potential insertion site may be used. For the VZV virus, an insertion site may be chosen from the group consisting of: TK, US3, gI, gE, gC, US3-gI intergenic region.

It will be understood that the gD gene, within a cassette as defined above irrespective of its origin, may be inserted into MDV, or another virus of the same type, in place of the gD gene itself or in another insertion site.

The subject of the present invention is preferably a herpesvirus chosen from the group consisting of VZV and serotypes 1, 2 and 3 MDV, expressing a gD glycoprotein during its replication in vitro.

The subject of the present invention is the in vitro production of infectious viruses, in particular HVT and MDV, in the form of free virions present in the cell culture supernatant. The culture techniques are, in particular, those customarily used in practice for a given virus. They are well known to a person skilled in the art and do not need to be described in greater detail here. The use of the transformed viruses according to the invention in the production of viruses facilitates the manufacture of vaccines, in particular those against Marek's disease, and of recombinant viruses, in particular HVT and MDV, while making it possible to obtain a more rapid generalized cytopathic effect (2 to 3 days depending on the strength of the inoculum) and a better resistance of the virus to preservation operations by freezing or by lyophilization. High titres of free viruses in the culture supernatant are advantageously obtained, in comparison with what is obtained in the absence of expression of gD. This is a noteworthy result.

The subject of the invention is hence a method for the culture of herpesvirus naturally deficient in gD, in which the virus which has been transformed by genetic recombination to express the gD glycoprotein is cultured on cells, and the virions produced are then collected in the culture supernatant. The techniques of virus culture are, in particular, those customarily used in practice. A person skilled in the art is entirely familiar with the techniques appropriate to each virus, and they do not need to be described in greater detail here.

The subject of the invention is also herpesvirus cultures capable of being obtained by this method. These cultures are characterized, in particular, in that they comprise the virus, in particular MDV, HVT, VZV, in the state of free virion, that is to say not associated with cells, and display the properties and qualities already stated.

The subject of the present invention is also the in vitro production of infectious viruses, in particular HVT or MDV, which may be used as expression vectors for foreign genes, especially for genes or fractions of genes coding for antigens inducing a protection against diseases, especially a protection of farm-bred fowl against pathogenic viruses, bacteria or parasites responsible for avian diseases, more especially chickens.

The subject of the invention is hence also the herpesviruses as defined above, which comprise, in addition, at least one heterologous gene inserted into their genome so that this gene may be expressed in vivo. To this end, the recombinant virus can comprise either a double cassette including the gD gene, the promoter of the latter and the gene coding for the antigen with a suitable promoter it being possible for the cassette to be inserted into the gD site for a virus such as MDV or into another site, or a cassette for each gene, the one comprising the gD gene which can be inserted, for example, into a site other than the natural gD site in the case of a virus such as MDV, and the other cassette can be inserted, for example, into the natural gD site or into any other suitable site, or alternatively only the natural promoter of the gD gene is replaced, and the cassette comprising the heterologous gene is inserted into another suitable site.

It is striking to note that, when the virus such as MDV has been transformed to express an endogenous gD gene or a gD gene of another serotype under the control of an effective promoter according to the invention, this inserted gene is expressed in vivo during viraemia and not only in the feather follicles (as in the case of the natural gD), which manifests itself in a stronger and earlier immune response, especially cellular immune response.

A further subject of the present invention is the production of vaccines which can advantageously be used via the aerial (nasal, ocular) oral or parenteral routes, in particular for immunizing chickens against Marek's disease and the other diseases corresponding to the specific antigens expressed by recombinant HVT or MDV viruses.

The vaccines according to the invention are characterized in that they comprise a live virus as is defined above, and in that they can be, in particular, in lyophilized or frozen form.

The method for the production of a live vaccine according to the invention is characterized in that a herpesvirus naturally deficient in gD, which has been transformed to express gD during its replication in vitro and, where appropriate, transformed to express in vivo at least one heterologous gene coding for a vaccinal antigen or immunogen, is cultured on cells.

The subject of the present invention is also the production of vaccines which can be administered in ovo to vaccinate chickens against Marek's disease, and the vaccines obtained.

Specifically, the subject of the present invention is the use of the gD gene as an insertion locus for constructing recombinant avian herpesviruses, in particular HVT or MDV, expressing, in addition, foreign genes of vaccinal interest.

The subject of the present invention is also the obtaining of infectious avian viruses, in particular HVT or MDV, capable of serving as vectors for the expression of foreign antigens and permitting vaccination in ovo.

The subject of the present invention is also a method for the vaccination, in particular, of farm-bred fowl, using the transformed viruses according to the invention and providing, in particular, for their administration via the aerial route, although the other routes are not ruled out.

Lastly, the disclosure of the principle underlying the invention enables a person skilled in the art to look also for natural mutants expressing gD in vitro in viruses of the MDV type. These mutants thus fall within the scope of the invention.

The invention will now be described in greater detail by means of examples of implementation, reference being made to the drawing, in which the following are seen:

in FIG. 1: by digestion of plasmid pRD001 comprising a 29 kbp fragment of HVT DNA, construction of plasmids pRD006 and pRD007 which comprise, respectively, a 2.8-kb fragment including the portion of gD on the 5' side of PstI and a 5.7 kb fragment including the portion of gD on the 3' side of PstI;

in FIG. 2: construction of plasmid pRD015 comprising the flanking portion at the 5' end of gD, from plasmid pRD001;

in FIG. 3: plasmid pRD022 obtained from the vector pBS-SK+ and comprising the gD gene lacking its portion on the 5' side of the SacI site;

in FIG. 4: plasmid pRD030 comprising the whole of the gD gene and restriction sites flanking it;

in FIG. 5: from pCMVβ, construction of plasmid pRD031 containing the gD gene under the control of the HCMV IE promoter, by replacement of the LacZ gene by gD;

in FIG. 6: plasmid pRD040 comprising a cassette including the gD gene and the HCMV IE promoter, in the vector pBS-SK+;

in FIG. 7: construction of plasmid pRD041 obtained by adding the 5' flanking sequence contained in plasmid pRD015 to plasmid pRD040;

in FIG. 8: construction of plasmid pRD043 comprising the gD gene, the HCMV promoter and the SV40 promoter/LacZ gene assembly supplied by pSVβ in pRD041 between the HCMV promoter and the 5' flanking sequence;

in FIG. 9: construction of plasmid pRD046 from plasmid pBamB containing an HVT BamHI fragment B including the TK gene;

in FIG. 10: construction of plasmid pRD051 by introduction of a multiple restriction site into the unique DraIII site of plasmid pRD049;

in FIG. 11: construction of plasmid pRD053 comprising the HCMV promoter/ HVT gD gene cassette inserted into the TK gene of HVT.

EXAMPLES

All the techniques used for the constructions of donor plasmids are standard techniques of molecular biology described by Sambrook et al. (Molecular Cloning :A Laboratory Manual, 2nd Edition, New York, Cold Spring Harbor Laboratory, 1989). The content of this publication is considered to be incorporated by reference in this description.

Example 1

This example had the dual objective of demonstrating, on the one hand the expression of gD in the epithelium of chicken feather follicles, and on the other hand that, according to the invention, the non-expression of gD in vitro is indeed linked to the natural promoter and may be obtained by replacement of the natural promoter by another promoter.

Feathers and tissues:

Day-old Rhode Island Red chicks (HPRS RIR) received 1000 pfu (plaque forming units) of an MDV strain RB1B or HPRS16, and the feathers, bursae, thymus and spleens were removed 4 to 6 weeks after inoculation. The same tissues originating from uninfected SPF chickens served as controls.

Feathers obtained from the dorsal and pectoral regions were held at the proximal end, and the feather tips approximately 0.5 cm in length were chopped with scissors and suspended in PBS or in an extraction buffer (5 mM dithiothreitol, 50 μg/ml PMSF, 1.5% sarkosyl). As a general rule, 20 feather tips were used per ml of buffer. After incubation for 24 to 36 hours at 4° C., the preparations were treated with ultrasound (3×30 s) and centrifuged at 10,000 rpm in a microcentrifuge. The supernatants, usually containing 2 μg of protein per μl , were used for a Western blot analysis.

The antigens were extracted from the bursae, thymus and spleens using the same buffers as those used for the feathers.
CECs infected with a vaccinia-gD recombinant:

Chick embryo fibroblasts (CECs) were infected with a vaccinia-gD recombinant (vaccinia virus containing the gD gene inserted into a site which is non-essential for its replication and under the control of an endogenous vaccinia promoter) at a multiplicity of infection of approximately 1 pfu/cell, and were harvested 3 to 4 days later when the cpe (cytopathic effects) were very pronounced. The cells were scraped off, washed rapidly in PBS and treated with ultrasound in PBS at a concentration of $2 \times 10^7$ cells/ml.
Western blotting:

Samples intended for Western blot analysis were brought to the boil in a denaturing buffer and 10 µg of feathers or tissues were applied per well (or lane). In the case of CECs infected with vaccinia-gD, only 4 µg were applied per well. The polypeptides were separated by electrophoresis on 12% acrylamide gel using a Biorad minigel apparatus and were transferred on to nitrocellulose (Hybond C, Amersham). After transfer, the polypeptides were stained with Ponceau red and photographed to check that the amounts of protein applied to each well were comparable.

The blots were rinsed with PBS, blocked with 5% skimmed milk in PBST (25 mM Tris pH 7.6, 0.14M NaCl and 0.05% Tween 20) and washed 4 times in PBST, for 5 minutes each time. They were then treated with a hybridoma DA7 (specific for gD) supernatant diluted to 1/50 in PBS containing 1% of BSA, for 1 h at room temperature. After 4 washes in PBST, the blots were incubated with anti-mouse goat IgG conjugated to peroxidase (Sigma), diluted to 1/1000 in PBST, and bound antibodies were detected by chemoluminescence (Dupont chemoluminescence reagent for Western blotting, Dupont). X-ray-sensitive films were exposed for 30 seconds to 1 minute according to the standard technique.
Immunofluoroescence test:

Skin sections prepared with a microtome (Cryostat) were fixed in acetone for 10 min at room temperature. They were dried in the air and treated with 5% BSA in PBS for 30 min at room temperature to prevent non-specific reactions. Monoclonal antibody DA7 (dilution to 1/100 in 1% BSA in PBS) or monoclonal antibody BD1 (mouse ascites fluid specific for pp38/24, diluted to 1/1000 in 1% BSA in PBS) were then added for 1 h at room temperature. The slides were washed 3 times in PBS, for 15 minutes each time. Anti-mouse goat IgG conjugated to FITC, diluted to 1/100 in 1% BSA in PBS, were then added for 1 h at room temperature. The slides were washed 4 times in PBS, for 15 min each time, dipped into water, mounted in glycerol/PBS and examined under UV light using a fluorescence microscope.
Results:

Western blot analysis showed that the feather preparations originating from 3 different chickens infected with MDV reacted with monoclonal antibody DA7. The antibody recognized a poly peptide appearing in the form of a band at 55 kDa, which is in agreement with the expected size for gD and with the in vitro translation product of the MDV gD gene (Zelnik et al., J. Gen. Virol. 75, 2747–2753). Products of lower molecular weight (35 kDa and below) were visualized and might correspond to unglycosylated forms.

This demonstrates the expression of gD in feather follicles in chickens infected with MDV.

Extracts from uninfected chickens, of uninfected CECs and of CECs infected with vaccinia alone did not react with the DA7 monoclonal, demonstrating the specificity of the test. The extracts of CECs infected with the vaccinia-gD recombinant gave two bands, including a band corresponding to the 55 kDa band in the test with the feather extracts.

The specificity of the test was further checked by demonstrating that the monoclonal directed against pp38/24 did not react either with CECs infected with the vaccinia-gD recombinant or with uninfected CECs. In contrast, this monoclonal reacts well, as expected, with feather extracts from infected chickens and with CECs infected with MDV.

It was hence demonstrated that both feather preparations infected with MDV and CECs infected with the vaccinia-gD recombinant reacted with the anti-gD monoclonal, and hence that the expression of this gene was obtained in vitro.

Replacement of the natural promoter of the gD gene by another promoter hence enables gD to be expressed in vitro.

Example 2

Construction of plasmid pRD043

HVT virus strain FC126 was isolated in 1968 by Dr Witter of the Regional Poultry Research Laboratory (U.S.D.A., East Lansing, Mich. U.S.A.), in a flock of 23-week-old turkeys (R. L. Witter et al., Am. J. Vet. Res. 31, 525–538, 1970). It was then passaged 10 times through duck fibroblasts and thereafter underwent 9 further passages through SPF chick embryo fibroblasts. The DNA used originates from viruses which were subjected to a total of 23 to 24 passages from the original isolate.

It would also be possible to use, for example, the HVT strain registered at the ATCC under the reference VR584C.

Figure 1:
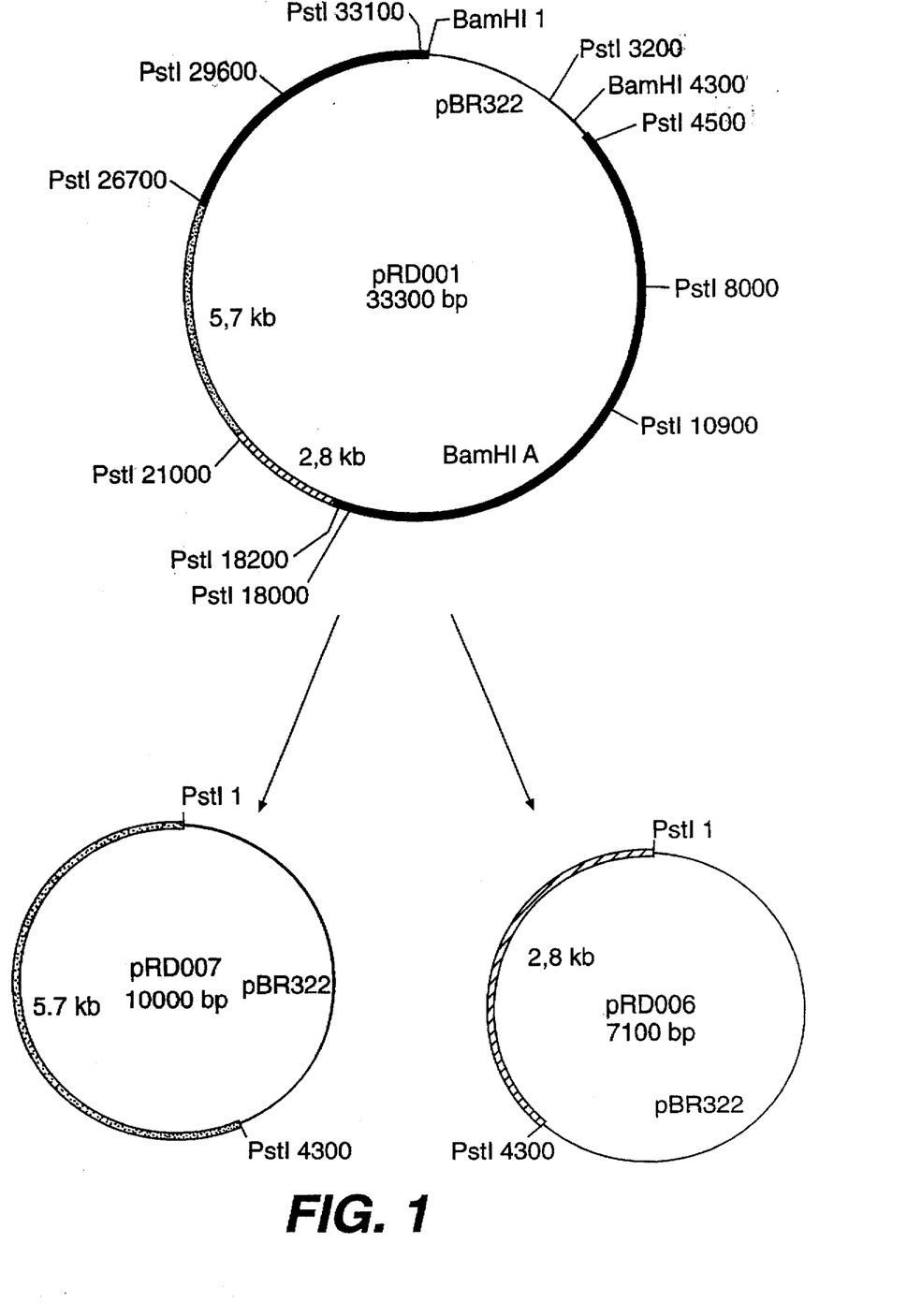
Figure 2:
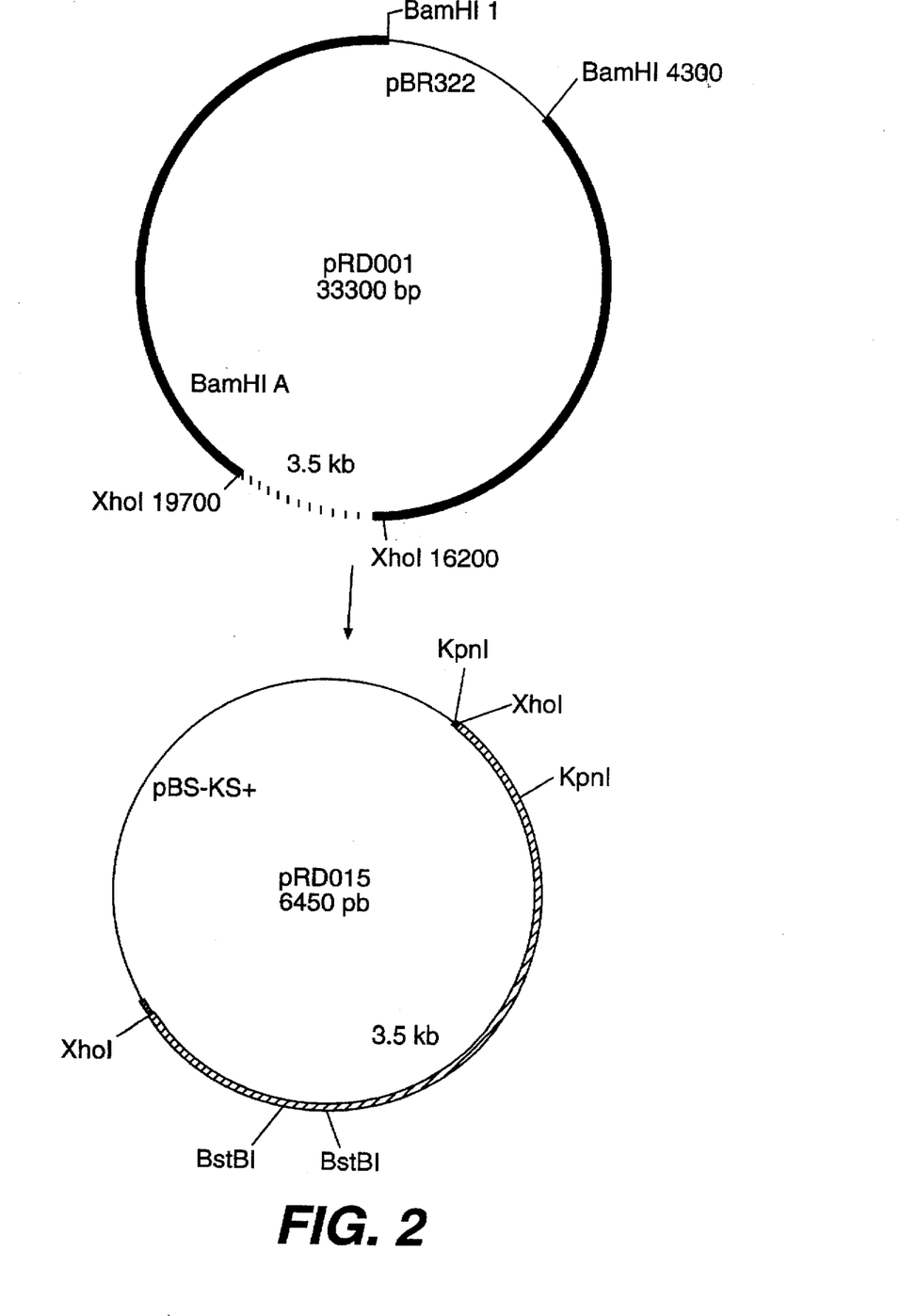
Figure 3:
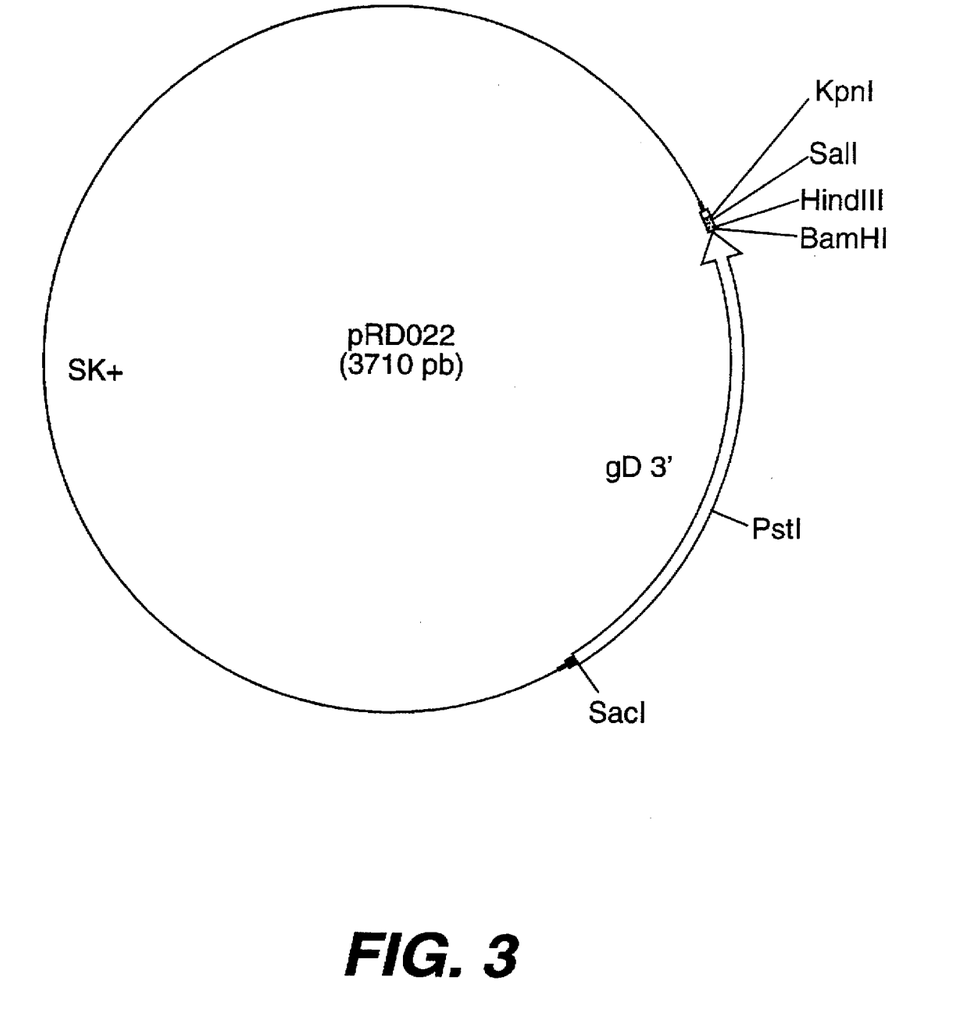

HVT virus genomic DNA was extracted according to the technique described by N. Ross (Ross L. J. N. et al., J. Gen. Virol. 1989, 70, 1789–1804, incorporated herein by reference). This DNA was digested with BamHI, and the 29-kbp fragment A (Igarashi T. et al., Virology 1987, 157, 351–358), comprising the Us region of HVT, was cloned into the vector pBR322 previously digested with BamHI, to give plasmid pRD001. pRD001 was digested with PstI, and the 2.8-kbp and 5.7-kbp PstI-PstI fragments were cloned into plasmid pBR322 digested with PstI, to give plasmids pRD006 and pRD007, respectively (FIG. 1).

pRD001 was digested with XhoI, and the 3.5-kbp XhoI-XhoI fragment was cloned into the vector pBluescript KS+ to give plasmid pRD015 (FIG. 2). Plasmid pRD006 was digested with SacI and PstI to isolate the 340-bp SacI-PstI fragment (fragment A). A PCR was carried out with the oligonucleotides RD045 (SEQ ID No. 1: 5' TGCTGGTAC-CGTCGACAAGCTTGGATCCGTGCA-GATAACACGTACTGGC 3') and pBR Pst- (SEQ ID No. 2:5' CATGTAACTCGCCTTGATC 3') and the template pRD007 to amplify the 3' region of the gD gene (positions 6491 to 6980 on the HVT Us sequence (Zelnik V. et al., J. Gen. Virol. 1993, 74, 2151–2162 incorporated herein by reference). The 560 bp PCR fragment was then digested with PstI and KpnI to isolate a 520-bp PstI-KpnI fragment B. Fragments A and B were cloned into the vector pBS-SK+ previously digested with SacI and KpnI, to give plasmid pRD022 (FIG. 3) comprising the gD gene lacking a 5' portion.

Figure 4:
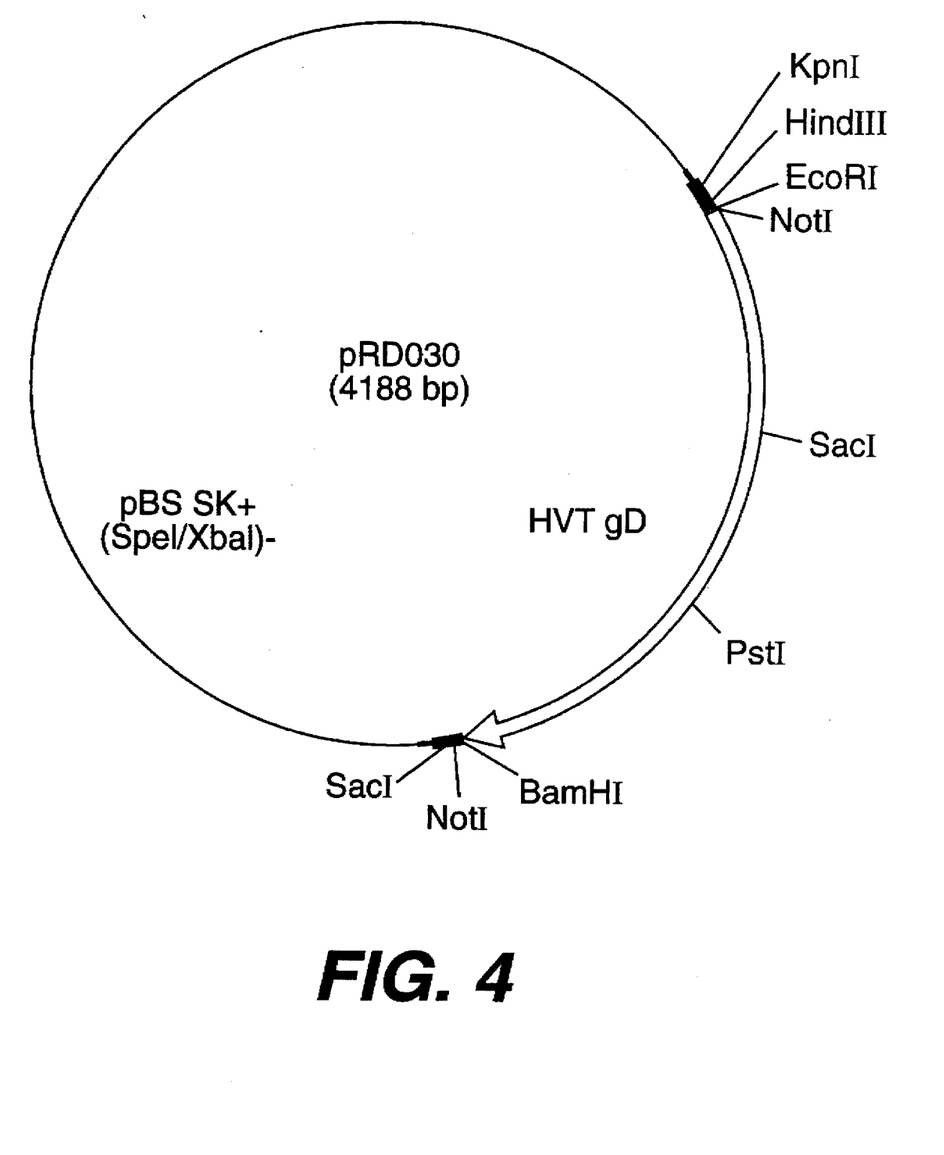

Plasmid pRD022 was digested with BamHI and SacI to isolate the 850-bp BamHI- SacI fragment (fragment C). A PCR was carried out with the oligonucleotides RD050 (SEQ ID No. 3:5' TGCTGAATTCGCGGCCGCATGATTAT-TGTCACCACTTC GAAGATGGC 3') and HVT40M1 (SEQ ID No. 4:5' GTCCCCGTTGA-CAACTACTA 3') and the template pRD006 to amplify the 5' region of the gD gene (positions 5747 to 6286 on the HVT Us sequence (Zelnik V.

et al., J. Gen. Virol. 1993, 74, 2151–2162). The 560-bp PCR fragment was digested with EcoRI and SacI to isolate the 420-bp EcoRI-SacI fragment D. Fragments C and D were cloned into a modified vector pBS-SK+, no longer containing the XbaI and SpeI sites (pBS-SK+ digested with XbaI and SpeI, then ligated) and digested with EcoRI and BamHI, to give plasmid pRD030 (FIG. 4) comprising the gD gene.

Figure 5:
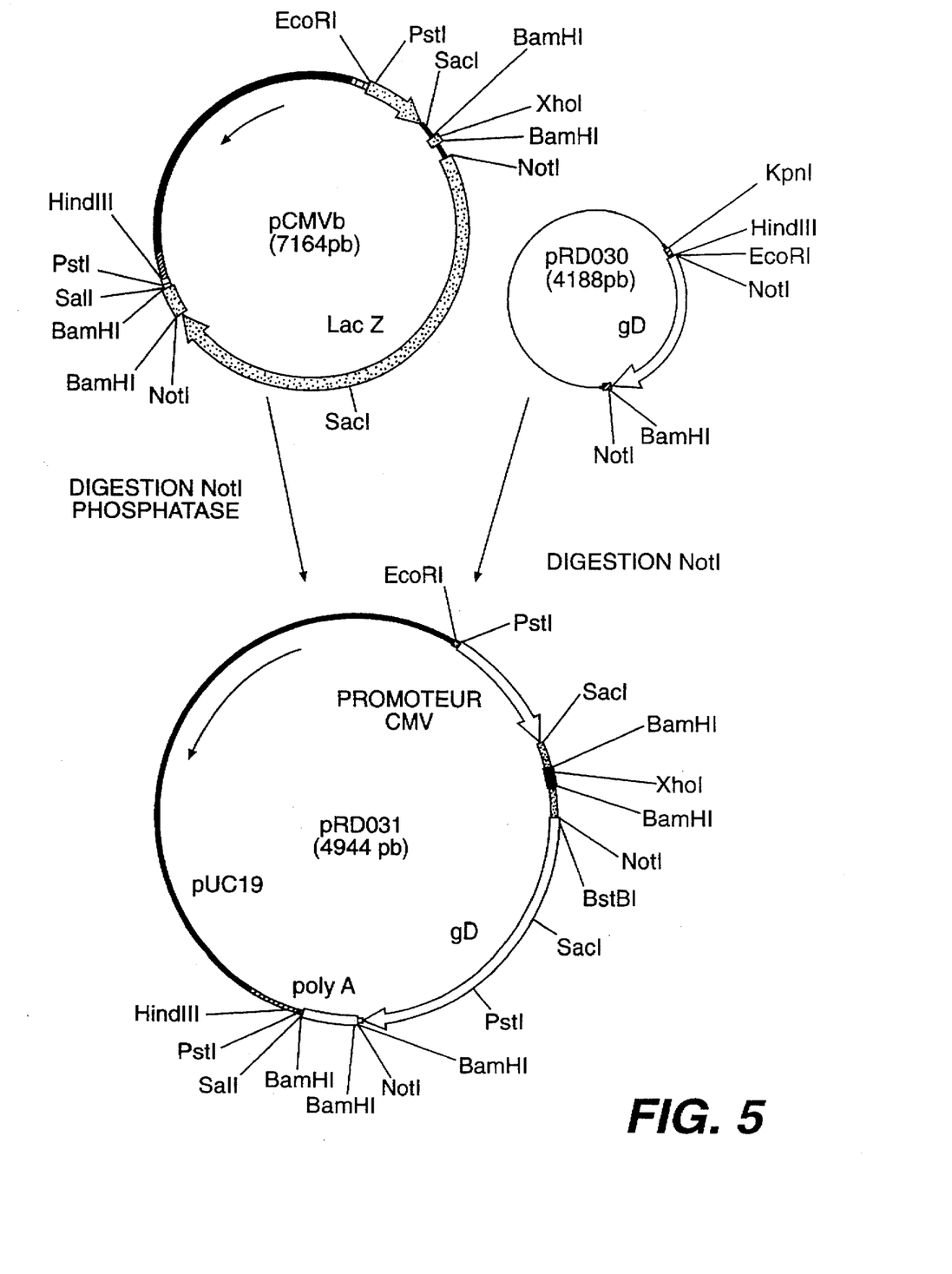

Plasmid pRD030 was digested with NotI to isolate the 1250-bp NotI-NotI fragment. This fragment was cloned into the vector pCMVβ (CLONTEC H Laboratories, Palo Alto, Calif.) digested with NotI for insertion of the gD gene in place of LacZ, giving plasmid pRD031 (4944 bp) containing the HVT gD gene under the control of the HCMV IE promoter (FIG. 5).

Figure 6:
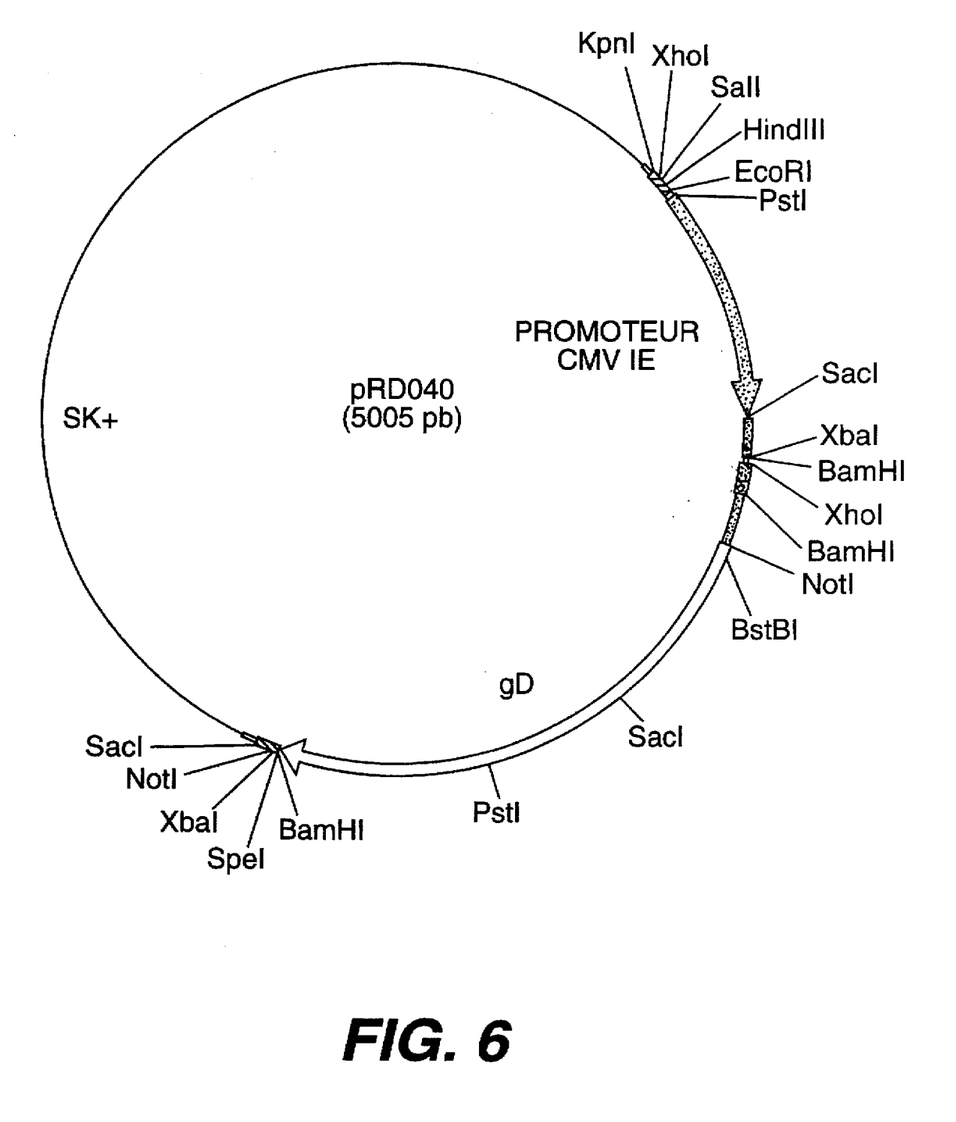

Plasmid pRD031 was digested, on the one hand with EcoRI and BstBI, and on the other hand with BstBI and BamHI, to isolate the 800-bp EcoRI-BstBI fragment and the 1250-bp BstBI-BamHI fragment, respectively. These two fragments were cloned into the vector pBS-SK+ digested with EcoRI and BamHI, to give plasmid pRD040 (FIG. 6) comprising the HCMV promoter and gD in the SK+ vector.

Figure 7:
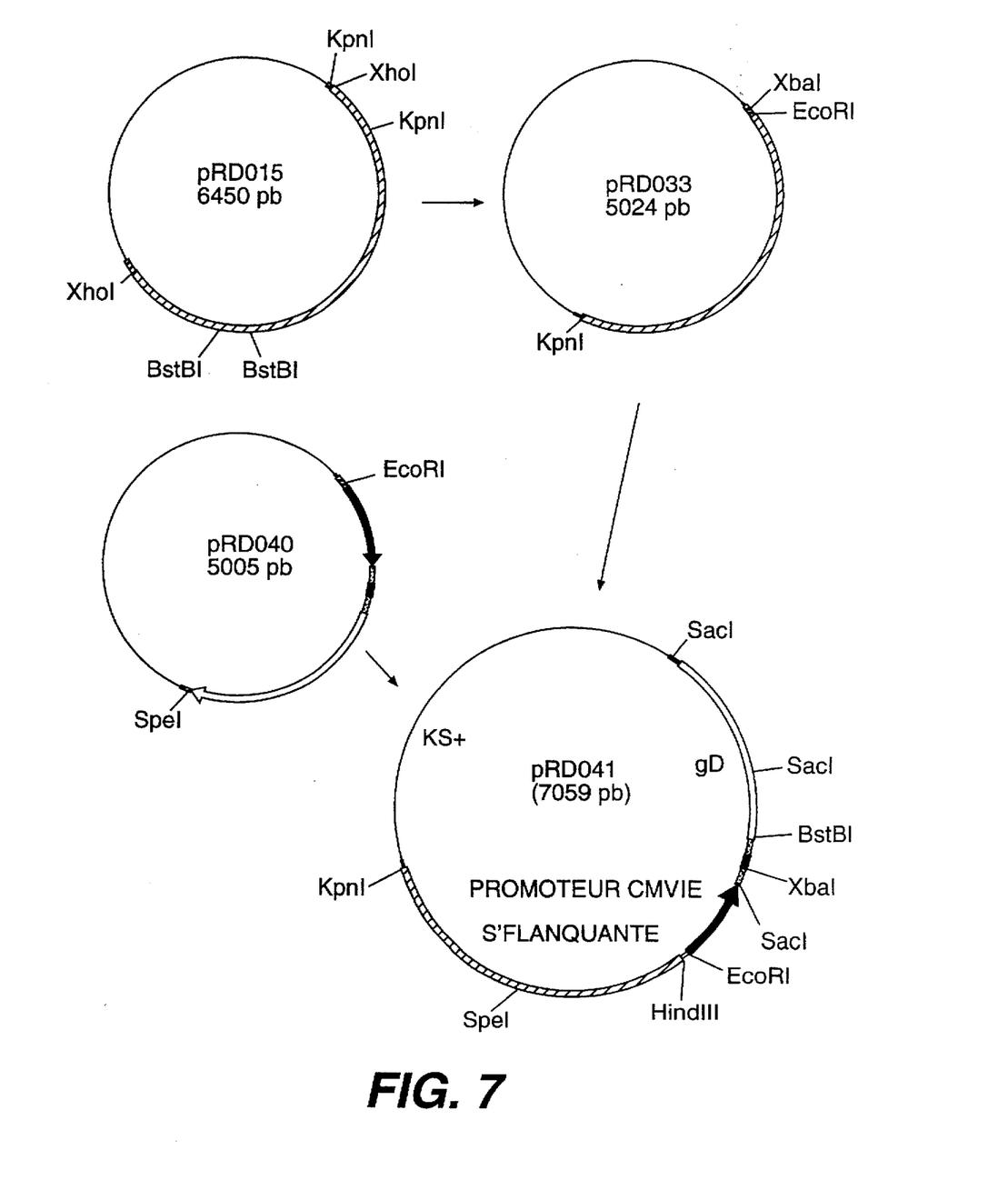

Plasmid pRD015 was digested with KpnI and BstBI to isolate a 2100-bp KpnI-BstBI fragment. This fragment was cloned into the vector pBS-KS+ digested with KpnI and ClaI, to give plasmid pRD033 (5024 bp). Plasmid pRD040 was digested with EcoRI and SpeI to isolate the 2000-bp EcoRI-SpeI fragment. This fragment was cloned into plasmid pRD033 digested with EcoRI and XbaI, to give plasmid pRD041 (FIG. 7) comprising gD, the HCMV promoter and the 5' flanking region.

Figure 8:
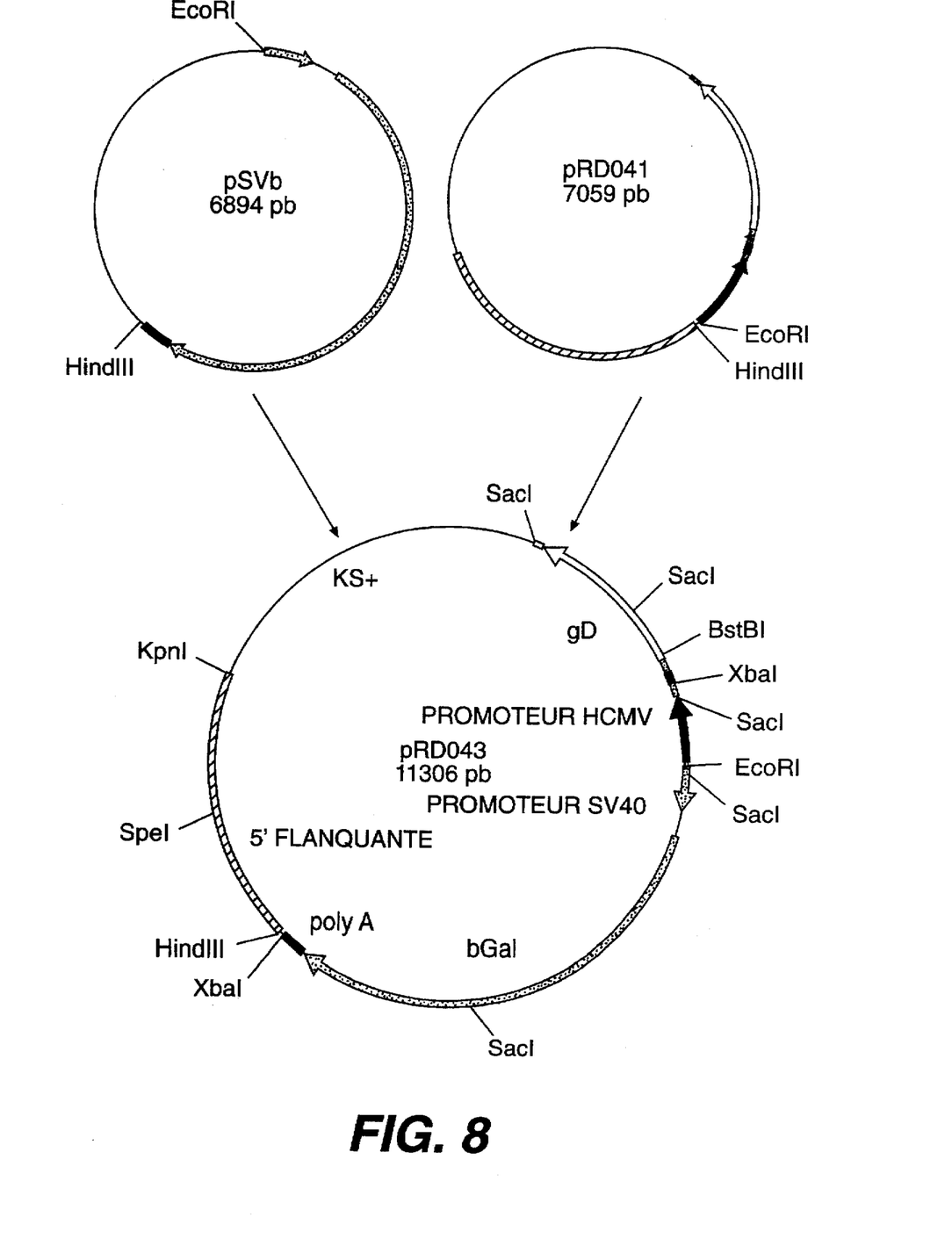

Plasmid pSVβ (CLONTEC H Laboratories, Palo Alto, Calif.) was digested with EcoRI and HindIII to isolate the 4300-bp EcoRI- HindIII fragment. This fragment was cloned into plasmid pRD041 digested with EcoRI and HindIII, to give plasmid pRD043 (11306 bp) (FIG. 8) comprising, in addition with respect to pRD041, the LacZ gene and its SV40 promoter.

Plasmid pRD053 makes it possible both to replace the natural promoter of gD by the HCMV IE promoter, and to introduce, by homologous recombination using the 5' arm corresponding to the fragment extending from bases 2152 to 4245 (Zelnik 1993-supra) (fragment corresponding to the larger portion of the sORF-3 gene, to the US2 gene and to the beginning of the US3 gene) and the 3' arm ranging from positions 5747 (A of the ATG of the gD gene) to 6980 (corresponding to the gD gene and to polyA).

It will be understood that, instead of supplying the LacZ gene, it would just as easily be possible to supply a gene coding for an antigen of interest.

Example 3: Construction of plasmid pRD053 (CMV-gD cassette in TK)

Figure 9:
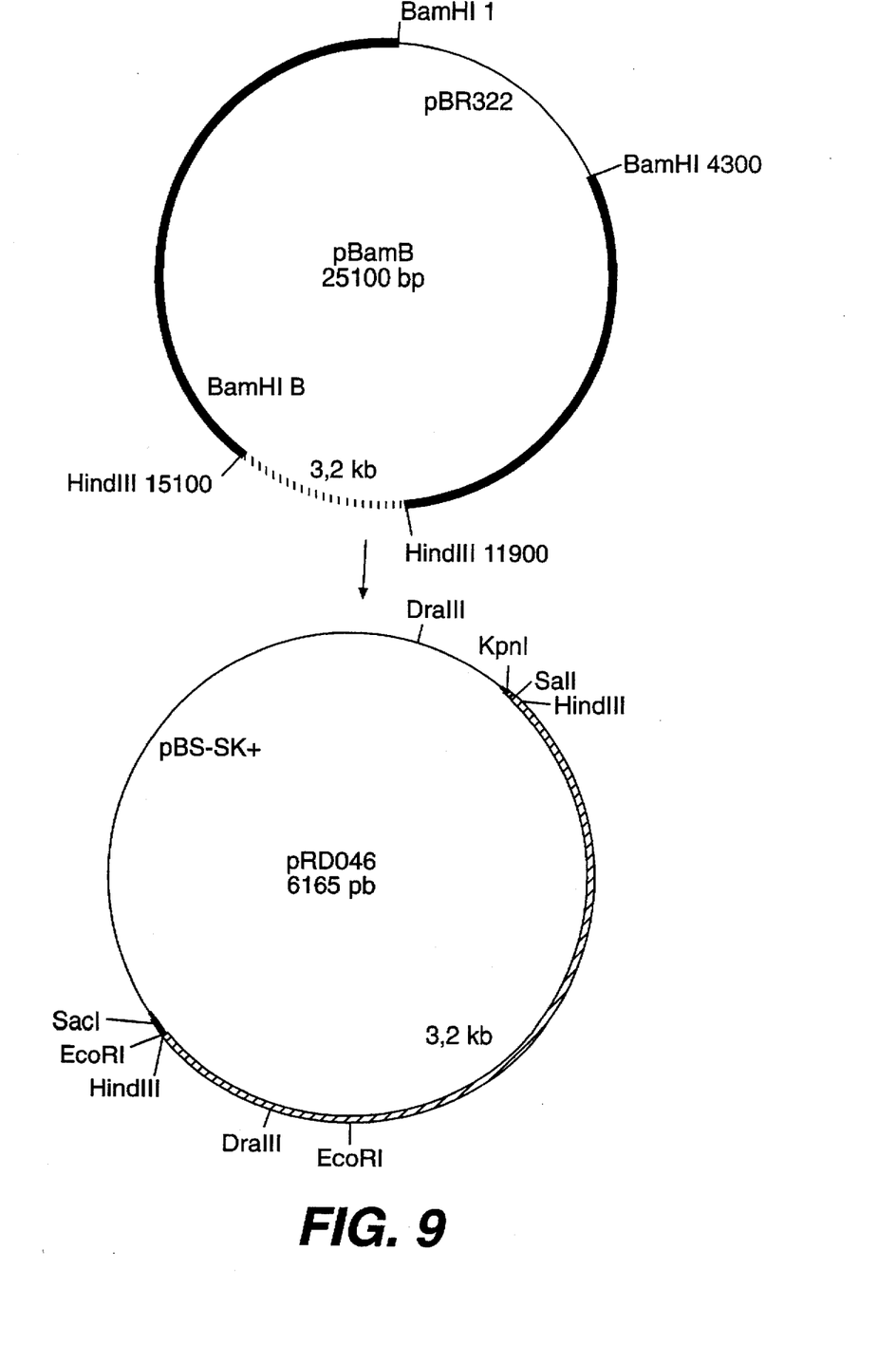
Figure 10:
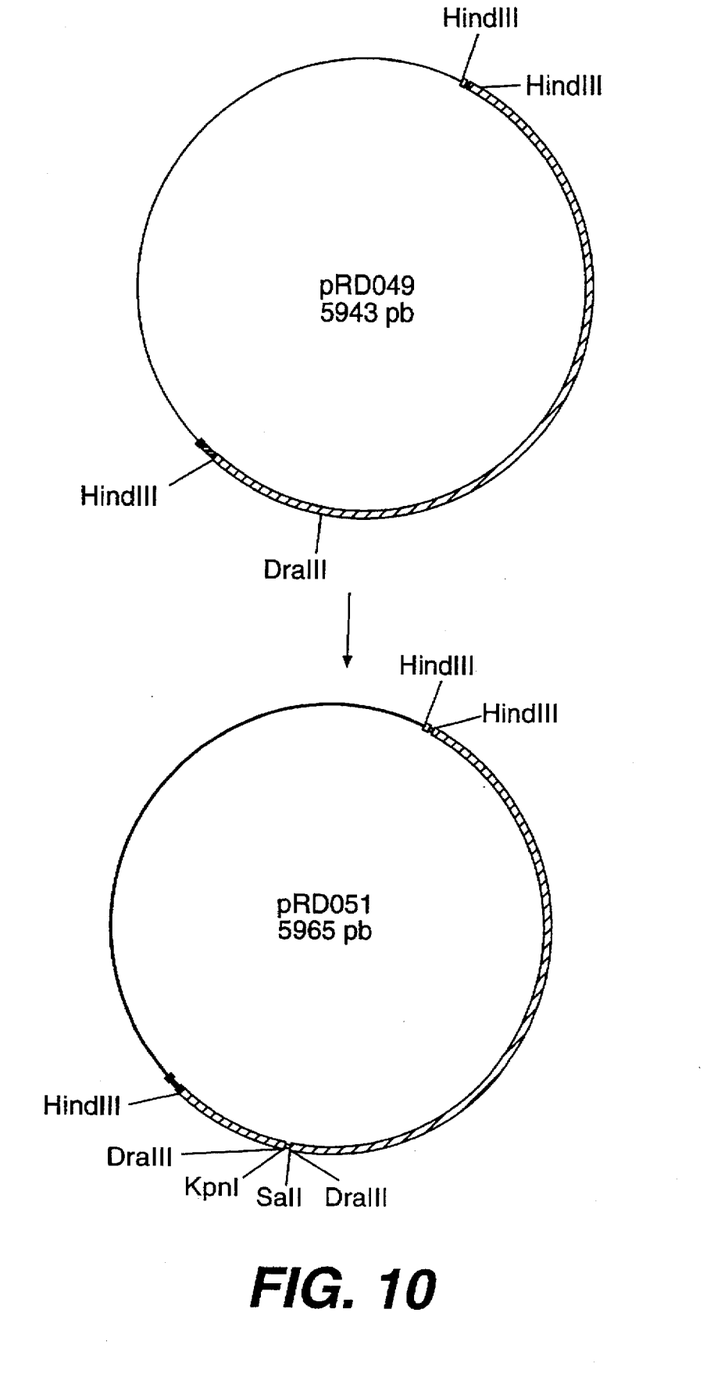

The HVT BamHI fragment B (Igarashi T. et al., Virology. 1987, 157, 351–358) containing the TK gene was cloned into the vector pBR322 to give plasmid pBamB. Plasmid pBamB was digested with HindIII to isolate the 3200-bp HindIII-HindIII fragment. This fragment was cloned into the vector pBS-SK+ digested with HindIII, to give plasmid pRD046 (FIG. 9). Plasmid pRD046 was digested with SalI, repaired with Klenow polymerase and then digested with SacI to isolate the 3200 bp SalI(K)-SacI fragment. This fragment was then ligated with the vector pUC18 previously digested with HindII and SacI, to give plasmid pRD049 (5943 b p). Plasmid pRD049 was then digested with DraIII (unique site on pRD049), dephosphorylated by the action of alkaline phosphatase and ligated with a double-stranded synthetic oligonucleotide obtained by hybridization of the following two oligonucleotides:

RD053 SEQ ID No. 5:5' GTGGTACCATAGTCGACAC-CCT 3'

RD054 SEQ ID No. 6:5' GTGTCGACTATGGTACCA-CAGG 3'

Figure 11:
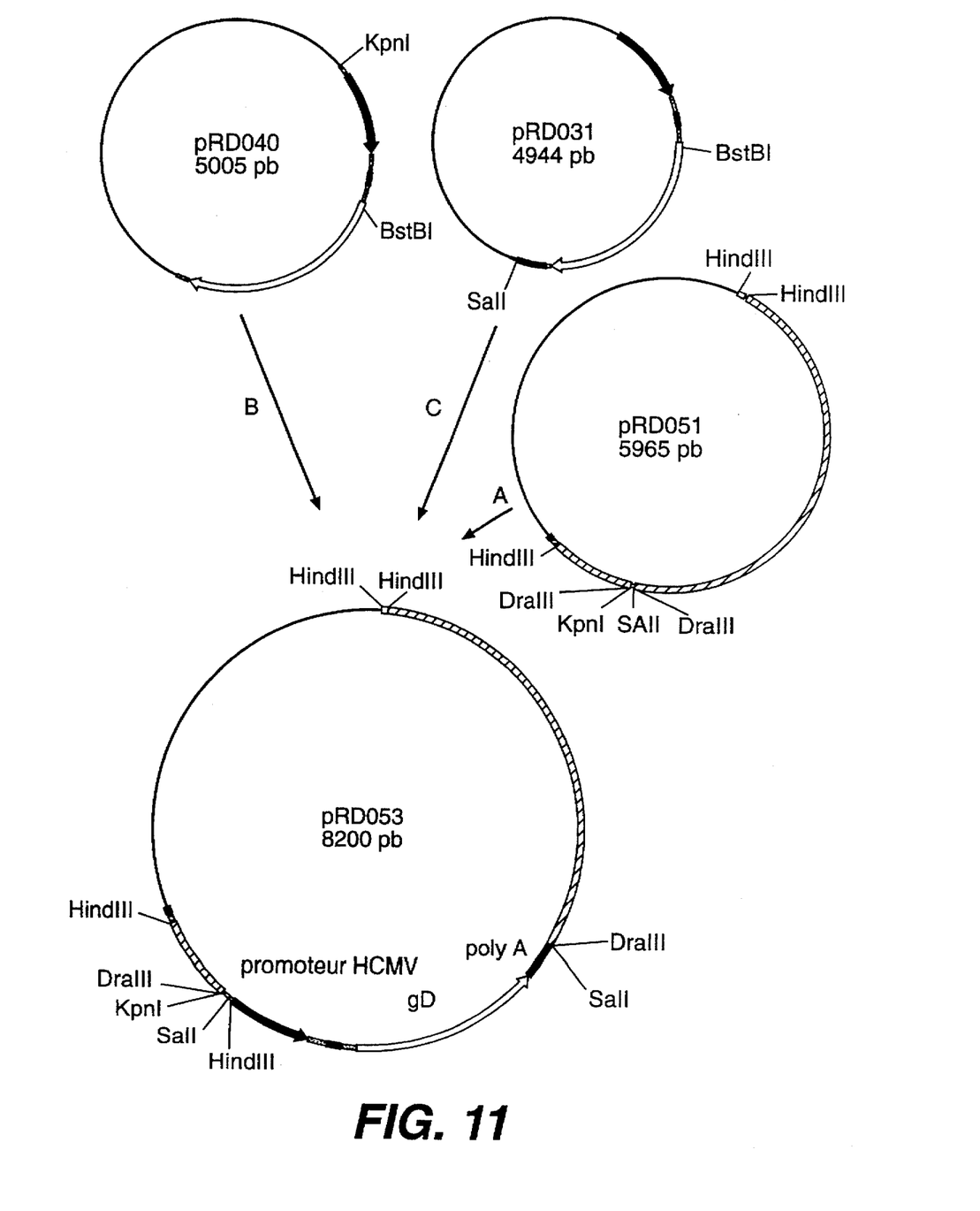

The plasmid thereby obtained was called pRD051 (FIG. 9). This plasmid was digested with KpnI and SalI to isolate the 5960 bp KpnI-SalI fragment (fragment A). Plasmid pRD040 (see Example 1) was digested with KpnI and BstBI to isolate the 800-bp KpnI-HCMV IE- ATG-BstBI fragment (fragment B). Plasmid pRD031 was digested with BstBI and SalI to isolate the 1450-bp BstBI-HVT gD-SalI fragment (fragment C). Fragments A, B and C were then ligated together to give plasmid pRD053 (FIG. 11) comprising the gD cassette inserted into TK.

This plasmid enables this gD cassette to be introduced into the TK gene by homologous recombination using 5' and 3' flanking arms which are, respectively, homologous with the regions upstream of the DraIII site of the TK gene (520-bp HindIII-DraIII fragment) and downstream of the DraIII site of the TK gene (2650-bp DraIII-HindIII fragment). This insertion leads to the inactivation of TK.

This plasmid is linearized with ScaI before cotransfection with HVT viral DNA.

Example 4

Isolation and purification of the recombinant virus vHVT004

The viral DNA used for transfection experiments was prepared according to the technique described by Robin Morgan (Morgan R. W. et al., Avian Diseases, 1990, 34, 345–351, incorporated herein by reference). Plasmid pRD043 was digested with KpnI for linearization, then extracted with a phenol/chloroform (19:1) mixture, precipitated with absolute ethanol and taken up in sterile water.

24-hour primary CEC cells were transfected with the following mixture: 5 µg of viral DNA +1 µg of the linearized plasmid pRD043 in 300 µl of OptiMEM medium (Gibco) and 100 µg of Lipofectamine (Gibco BRL Ref. 18324-012) in 300 µl of medium (final volume of the mixture=600 µl ). These 600 µl were then diluted in 3 ml (final volume) of medium and spread on $3.10^6$ CECs. The mixture is left in contact with the cells for 5 hours, then removed and replaced by 5 ml of culture medium. The cells are then left in culture for 3 days at 37° C., and they are thereafter pronased, mixed with fresh secondary CECs (3:1 mixture) and spread again on to Petri dishes until a cytopathic effect (CPE) appears. The cell lawn is then pronased and serves as inoculum (on the basis of 1 plaque per dish) for 60 mm dishes (containing $2.10^6$ secondary CECs). Three days after inoculation, a layer of agar is poured over the cell lawn. 24 hours later, an agar overlayer containing X-Gal (500 µg per ml final) is poured on. After three hours, an intense blue coloration develops in the plaques containing the recombinant viruses. Each blue plaque is then subcultured individually for amplification in a cavity of a 96-well plate. When a CPE appears, the cavity is pronased and serves as inoculum for a new 60 mm dish. Selection of the recombinant plaques and estimation of the percentage purification of these plaques are carried out as before by X-Gal staining of the plaques under agar. In general, 4 cycles of successive isolations are sufficient to obtain recombinant viruses all of whose progeny display the blue coloration. Each individual 100% purified plaque is then characterized at molecular level by PCR and Southern blot techniques using the appropriate oligonucleotides and DNA probes.

A 100% pure clone displaying the characters of the expected recombinant was isolated and designated vHVT004. This virus contains an SV40/LacZ cassette inserted between the US2 and gD genes, as well as the HCMV IE promoter placed directly upstream of the gD gene and thus controlling this gene in its original site. Hence US3, which is the insertion site, is deleted in this virus.

Example 5

Isolation and purification of the recombinant virus vHVT005 (TK–)

The HVT virus genomic DNA used for the transfection experiments was prepared as before (Morgan R. et al., Avian Diseases, 1990, 34, 345–351). Transfections were carried out with plasmid pRD053 linearized with ScaI as described in Example 3. After 3 days of culture, the cells are pronased, mixed with fresh secondary CECs and spread again on Petri dishes. When a CPE appears, the cell lawn is pronased and serves as inoculum for 60 mm Petri dishes. Culturing is then performed with a culture medium containing 1-β-D-arabinofuranosylthymine (ara T) (Sigma) at a final concentration of 100 µg/ml of culture medium. ara T inhibits the replication of TK+ HVT viruses, and only natural TK– mutants or TK– recombinants can replicate in the presence of ara T. Three days after infection, a layer of agar is poured over the cell lawn. After 24 hours, the viral plaques present on the cell lawn are subcultured individually in cavities of a 96-well plate. Culturing of these plaques is carried out in the presence of ara T in the culture medium. When a CPE appears, the cavities are pronased, dilutions of the infected cavities are spread on to Petri dishes and a new cycle of culture under agar is performed as before. After two cycles of culture in the presence of ara T, culturing may be performed in normal medium. Four cycles of isolation/purification are sufficient to obtain recombinant clones which are 100% pure for the TK– character. These clones are then characterized at molecular level with the usual techniques of molecular biology (PCR, Southern blotting, and the like).

A 100% pure clone displaying the characters of the expected recombinant was isolated and designated vHVT005. This virus contains the gD gene under the control of the HCMV IE promoter in the TK gene, which is hence inactivated.

We claim:

1. A herpesvirus naturally deficient in gD selected from the group consisting of serotypes 1, 2, 3 MDV virus and VZV virus, where said herpesvirus transformed to express a gD glycoprotein during its replication in vitro.

2. The herpesvirus according to claim 1 wherein the herpesvirus is selected from a serotype 1, 2, and 3 MDV virus.

3. The herpesvirus according to claim 1 wherein the herpesvirus is VZV virus.

4. A herpesvirus according to claim 2, characterized in that the gD gene of said herpesvirus is placed under the control of a promoter and said promoter is capable of inducing expression of the gD gene in vitro.

5. The herpesvirus according to claim 1, characterized in that said herpesvirus comprises an expression cassette containing a gD gene placed under the control of a promoter permitting expression of said gD gene in vitro.

6. The herpesvirus according to claim 5, characterized in that the expression cassette is inserted into a site which is non-essential for the replication of said herpesvirus and for the efficacy of said herpesvirus as vaccine.

7. The herpesvirus according to claim 6, characterized in that, for serotypes 1, 2 and 3 MDV, the insertion site for said expression cassette is chosen from the group consisting of US2, US3, US10, gI, gD, TK, UL13.

8. The herpesvirus according to claim 6, characterized in that, for VZV, the insertion site for said expression cassette is chosen from the group consisting of TK, US3, gI, gE, gC and US3-gI intergenic region.

9. The herpesvirus according to claim 4, characterized in that the promoter integrated to provide for the in vitro expression of a gD gene is a strong promoter such as the HCMV IE promoter or the SV40 promoter.

10. The herpesvirus according to any one of claim 1 to 2, characterized in that it comprises, in addition, at least one heterologous gene coding for an antigen of interest, inserted into its genome so that this heterologous gene may be expressed in vivo.

11. The herpesvirus according to claim 10, characterized in that it comprises an expression cassette comprising a gD gene and the heterologous gene, each with their own promoter, where said expression cassette is inserted into a non-essential site.

12. A vaccine comprising a live virus according to any one of claims 1–3.

13. The vaccine according to claim 12, characterized in that it can be used via the parenteral, oral or aerial routes.

14. The vaccine according to claim 12, characterized in that it is in lyophilized or frozen form.

15. A method comprising culturing on cells a herpesvirus according to claim 1 and collecting the virions produced.

16. A herpesvirus culture comprising a herpesvirus selected from the group consisting of serotypes 1, 2 and 3 MDV, obtained by the method according to claim 15.

17. A method for the production of a live vaccine, comprising culturing on cells a herpesvirus, according to claim 1, and collecting the virions produced.

18. The method according to claim 17, wherein the herpesvirus cultured is a serotype 1, 2 or 3 MDV virus transformed to express gD in vitro.

19. The herpesvirus according to claim 5, characterized in that the promoter included in said expression cassette is different from the natural promoter of the gD gene which is inserted.

20. The herpesvirus according to claim 5, characterized in that the promoter included in said expression cassette is the natural promoter of the gD which is inserted and said promoter originates from a virus naturally expressing said gD gene.

21. Herpesvirus culture comprising VZV virus, obtained by the method of claim 15.

22. Recombinant serotype 1, 2 or 3 MDV herpesvirus genetically transformed to express gD outside the feature follicle during its replication in vivo.

23. Recombinant VZV herpesvirus genetically transformed to express gD during its replication in vivo.

24. Method comprising culturing on cells a herpesvirus according to claim 1, which has been transformed to express gD during its replication in vivo and wherein said herpesvirus is also transformed to express in vivo at least one other heterologous gene coding for a vaccinal immunogen.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear     ( i i ) MOLECULE TYPE: DNA (genomic)

( i i i ) HYPOTHETICAL: NO

( i v ) ANTI-SENSE: NO

( x i ) SEQUENCE DESCRIPTION: SEQ ID NO:1:

```
TGCTGGTACC GTCGACAAGC TTGGATCCGT GCAGATAACA CGTACTGGC            49
```

( 2 ) INFORMATION FOR SEQ ID NO:2:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear     ( i i ) MOLECULE TYPE: DNA (genomic)

( i i i ) HYPOTHETICAL: NO

( i v ) ANTI-SENSE: NO

( x i ) SEQUENCE DESCRIPTION: SEQ ID NO:2:

```
CATGTAACTC GCCTTGATC                                             19
```

( 2 ) INFORMATION FOR SEQ ID NO:3:

( i ) SEQUENCE CHARACTERISTICS:
        ( A ) LENGTH: 47 base pairs
        ( B ) TYPE: nucleic acid
        ( C ) STRANDEDNESS: single ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:3:

TGCTGAATTC GCGGCCGCAT GATTATTGTC ACCACTTCGA AGATGGC    47

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:4:

GTCCCCGTTG ACAACTACTA    20

( 2 ) INFORMATION FOR SEQ ID NO:5:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:5:

GTGGTACCAT AGTCGACACC CT    22

( 2 ) INFORMATION FOR SEQ ID NO:6:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:6:

GTGTCGACTA TGGTACCACA GG    22